United States Patent [19]
Columbus

[11] Patent Number: 4,549,952
[45] Date of Patent: Oct. 29, 1985

[54] CAPILLARY TRANSPORT DEVICE HAVING MEANS FOR INCREASING THE VISCOSITY OF THE TRANSPORTED LIQUID

[75] Inventor: Richard L. Columbus, Rochester, N.Y.

[73] Assignee: Eastman Kodak Company, Rochester, N.Y.

[21] Appl. No.: 537,553

[22] Filed: Oct. 3, 1983

Related U.S. Application Data

[63] Continuation-in-part of Ser. No. 443,785, Nov. 22, 1982, abandoned.

[51] Int. Cl.$^4$ ............... G01N 1/00; G01N 27/28; G01N 33/48
[52] U.S. Cl. ............... 204/416; 137/13; 138/44; 141/31; 141/99; 204/435; 422/100
[58] Field of Search ............... 422/100, 58; 137/13, 137/D10, 251; 138/44, 45; 73/864.02, 864.72; 204/409, 416, 418, 435; 141/31, 99, 100

[56] References Cited

U.S. PATENT DOCUMENTS

| | | |
|---|---|---|
| 2,568,519 | 9/1951 | Smith ............... 138/45 |
| 3,482,943 | 2/1966 | Csizmas et al. . |
| 3,690,836 | 2/1967 | Buissiere et al. . |
| 3,715,192 | 2/1973 | Wenz et al. . |
| 3,864,979 | 2/1975 | Ayres ............... 422/100 X |
| 3,910,856 | 10/1975 | Kruka et al. ............... 137/13 X |
| 3,961,639 | 6/1976 | Chang et al. ............... 137/13 |
| 4,184,936 | 1/1980 | Paul et al. . |
| 4,203,440 | 5/1980 | Theeuwes . |
| 4,203,442 | 5/1980 | Michaels . |
| 4,233,029 | 11/1980 | Columbus ............... 422/58 X |
| 4,254,083 | 3/1981 | Columbus . |
| 4,271,119 | 6/1981 | Columbus . |
| 4,302,313 | 11/1981 | Columbus . |
| 4,310,399 | 1/1982 | Columbus . |

Primary Examiner—Arnold Turk
Attorney, Agent, or Firm—Dana M. Schmidt

[57] ABSTRACT

A capillary transport device is disclosed, suitable for use as an ion bridge for potentiometric test elements. Such device has an internal capillary transport passage, and two access apertures for separate access of two different liquids to two spaced-apart regions of the passage. To control the liquid flow rate within the passage, there is disposed on at least a portion of at least one of the surfaces of the passage between the two regions, means for (a) increasing the viscosity of the liquid while it is flowing past at least one surface, and (b) at the same time maintaining such flow continuous within the passage.

21 Claims, 6 Drawing Figures

CAPILLARY TRANSPORT DEVICE HAVING MEANS FOR INCREASING THE VISCOSITY OF THE TRANSPORTED LIQUID

This is a continuation-in-part of application Ser. No. 443,785, filed Nov. 22, 1982, now abandoned.

FIELD OF THE INVENTION

This invention relates to a capillary transport device useful with ion-selective electrodes, wherein liquid is transported through a capillary passage that is within the device.

BACKGROUND OF THE INVENTION

My U.S. Pat. No. 4,271,119, issued June 2, 1981, describes a potentiometric test device comprising one or more pairs of ion-selective electrodes and an ion bridge in liquid communication with the paired electrodes, FIG. 10. The ion bridge features an internal capillary liquid transport passage formed by two opposed transport surfaces spaced apart a distance effective to induce capillary flow of liquid between the surfaces. Two access apertures are provided to allow both a patient sample and a reference liquid to be introduced into the bridge. Each of the liquids flows into contact with one-half of the paired electrodes on one side of the ion bridge, and into contact with the other liquid at a junction located in a portion of the passage between the two access apertures.

The aforesaid device has proven to be a highly effective device for assaying ionic analytes. There are, however, several aspects which have warranted further improvement.

First of all, the device is intended to be used by simultaneously metering the reference liquid and a patient's body liquid, e.g., serum, at each of the two access apertures, so that the two liquids simultaneously enter the bridge. On occasion, the simultaneous metering does not occur. Unless delay means are provided, such as the gating walls 110 of the device of my aforesaid patent, FIG. 10, flow of one liquid within the bridge occasionally is so rapid (2 seconds or less to flow a distance of about 1 cm) that it reaches the other access aperture before the second liquid is metered. Although walls 110 are effective in providing a delay, there are certain constructions of the bridge which do not readily lend themselves to the incorporation of such gating walls. A reduction in capillary spacing is known to provide a reduced flow rate, but such reduced spacings as fixed dimensions formed by plastic parts, are disadvantageous because (a) they provide only a gradual withdrawal of liquid from the access aperture and (b) narrow spacings are difficult to manufacture within desired tolerances. A gradual withdrawal of the liquid deposited at the liquid access aperture introduces the possibility that, while it is occurring, a portion of the liquid will be splashed out of the access aperture if the test element is inadvertently jarred or bumped.

Second, under extreme conditions, it is possible that the surface tension of the patient sample will be markedly different from that of the reference liquid. If that is the case, it has been found that the liquid with the higher surface tension produces a driving force that can overcome the flow of the other liquid. If the other, lower surface tension liquid is not deposited in the proper sequence relative to the higher surface tension liquid, in some instances the higher surface tension liquid pushes the lower surface tension liquid entirely out of the bridge, up through the access aperture. This causes contamination of the electrode of the lower surface tension liquid, by the higher surface tension liquid.

SUMMARY OF THE INVENTION

I have discovered that the aforementioned problems of too-rapid flow, or of displacement of the lower surface tension liquid by the higher surface tension liquid, are overcome by increasing the viscosity of liquid while it flows within the capillary passage, in such a manner that the integrity of the flow continues to be maintained. The increased viscosity is effective both to reduce the flow rate and prevent subsequent displacement of the junction that forms between two liquids introduced into the passage.

More specifically, there is provided a liquid transport device for simultaneously transporting two different liquids within a capillary passage. The device comprises two opposed liquid transport surfaces spaced apart a distance effective to induce capillary flow between the surfaces of introduced liquid and to create the capillary passage, and access means, including two apertures, for respectively admitting the different liquids to the passage from the exterior of the device to two spaced-apart regions of the passage. In accordance with one aspect of the invention, the device is improved in that there is disposed on at least a part of at least one of the surfaces, control means for (a) increasing the viscosity of the liquid while it is flowing past at least one surface, and (b) at the same time maintaining such flow continuous within the passage.

In accord with another aspect of the invention, the control means comprises a water-swellable composition disposed on the surface of the capillary passage.

In accord with yet another aspect of the invention, the device is improved in that such water-swellable composition is water-swellable by an amount and at a rate sufficient to reduce the initial capillary spacing by at least about 25% by the time the liquids flow together within the passage to form a junction.

Thus, it is an advantage of the present invention that the device of the invention reduces the rate of liquid flow within it, so as to prevent one of the two liquids used therewith from flowing too fast, for example, so fast that it contaminates the electrode in an ISE test element that is intended for the other liquid.

It is a further advantage of the present invention that the device prevents a higher surface tension liquid from pushing a lower surface tension liquid away from the normal junction area of the device.

It is a related advantage of the invention that the aforementioned advantages are achieved without the need for severe manufacturing tolerances in the dimensions of plastic parts.

Other features and advantages will become apparent upon reference to the following Description of the Preferred Embodiments, when read in light of the attached drawings.

DESCRIPTION OF THE PREFERRED EMBODIMENTS

Figure 1:
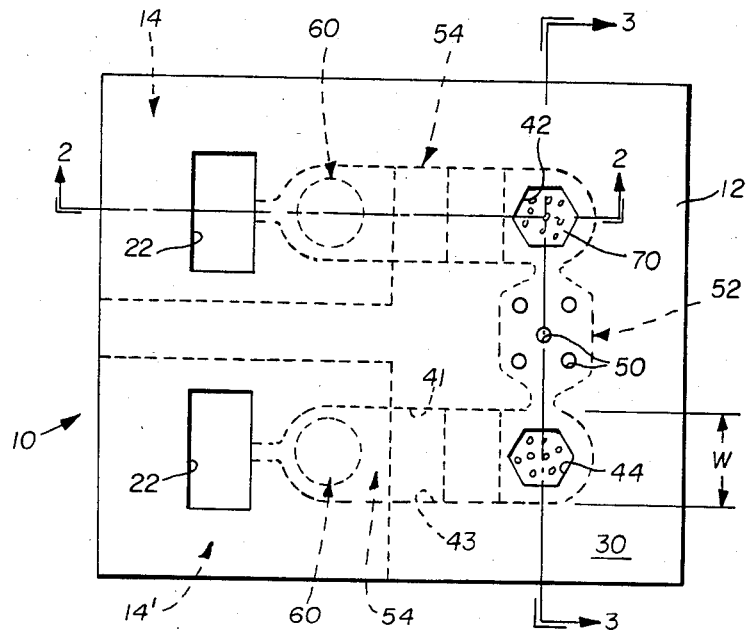
FIG. 1 is a plan view of a device constructed in accordance with the invention.

The preferred embodiments hereinafter described refer particularly to the use of the invention in an ion bridge for the potentiometric detection of ionic analytes. In addition, it is applicable to any transport device using a capillary passage wherein two different liquids are simultaneously transported to meet at a junction.

The ionic analytes, commonly called electrolytes, are those present in any liquid, whether biological or industrial. The device of the invention works particularly well for biological liquids such as serum, urine and spinal fluid having surface tensions between about 25 and about 75 dynes/cm$^2$.

The device 10 shown in FIG. 1 comprises an electrically insulative frame 12 which mounts a spaced-apart pair of preferably planar, solid ion-selective electrodes 14, 14' (hereinafter, "ISE's"). The ISE's are preferably adhered to exterior surface 13 of device 10 by an adhesive, formed in a layer 15, FIG. 2. As described in U.S. Pat. No. 4,053,381, issued on Oct. 11, 1977, the details of which are expressly incorporated herein by reference, each ISE is a generally flat multilayered element comprising adjacent layers 16–20. (The layer thicknesses are exaggerated in FIG. 2 for clarity.) Each layer 16 is an ion-selective membrane containing an ionophore and a solvent. When a drop of sample liquid or reference fluid makes contact, the ion of choice is carried by or otherwise effectively penetrates through layer 16 to the underlying layers 17–18. At these layers, an electrical potential is generated proportional to the activity of that particular ion. Layer 17, for example, is a dried hydrophilic binder containing the salt $X^{\oplus}Z^{\ominus}$, where $X^{\oplus}$ is the analyte to be measured. Layer 18 in such instances is the $Z^{\ominus}$ salt of an electrically conductive metal $M^{\oplus}$, and metal $M°$ forms layer 19. Layer 20 is an insulative support. Because layer 19 is electrically conductive, a potential is detectable by an electrometer, not shown, via probes which penetrate through layer 18 into contact with layer 19 at windows 22 in frame 12, FIG. 1. Any difference in these potentials due to two different ionic activities of the ion of choice in the two liquids is registered as a difference potential on the electrometer. This reading then is converted into a measure of concentration of the ionic analyte.

Useful embodiments include those in which one or more of layers 16–19 are altered, omitted, or added to. For example, if ISE 14 is constructed to test for $Cl^{\ominus}$, the laminated layers are as follows: a polyethylene terephthalate support, and a layer thereon of $Ag°$ over which a layer of silver chloride is formed. A top layer of cellulose acetate, containing a surfactant and polyethylene glycol, is added as described in U.S. Pat. No. 4,199,411, issued on Apr. 27, 1980, for the purpose of removing bromide interference.

Figure 2:
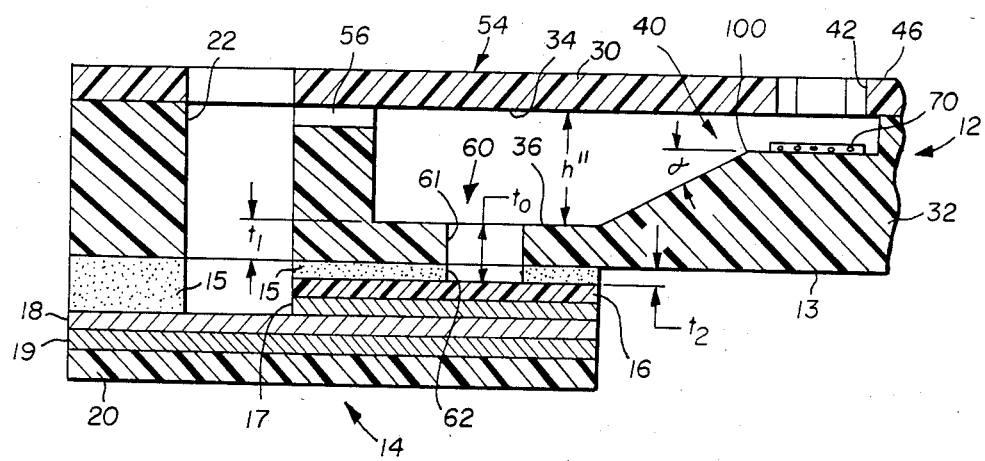
FIG. 2 is a fragmentary section view taken generally along the line 2—2 of FIG. 1.

Frame 12 is formed by a pair of members 30 and 32, FIG. 2, having opposing internal surfaces 34 and 36, respectively, which comprise the transport surfaces for the liquids. Member 30 has an exterior surface 46. Surfaces 34 and 36 are spaced apart a distance effective to provide capillary flow of introduced liquid and to form a capillary transport passage 40, in the manner described in U.S. Pat. No. 4,302,313. The contents of that patent are expressly incorporated herein by reference. The capillary spacing providing the capillary flow is preferably no greater than about 600 microns.

In addition to the opposing surfaces 34 and 36, passage 40 is further defined by sidewalls 41 and 43, FIG. 1, past which the liquid flows. The flow-through width of passage 40 is measured between these sidewalls. Alternatively, an exposed edge will act as a flow-terminating means, as is described in my U.S. Pat. No. 4,254,083, col. 3. Such an edge is obtainable by vertically slicing the device 10, FIG. 1, along a plane coinciding with the plane of outer walls 43, to provide a flow-terminating means that defines flow-through width w.

Figure 3:
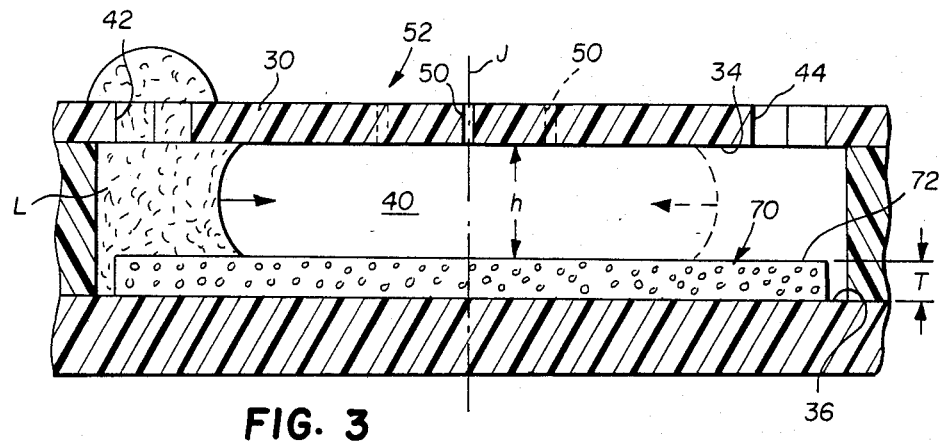
FIG. 3 is a fragmentary section view taken generally along the line 3—3 of FIG. 1.
Figure 4:
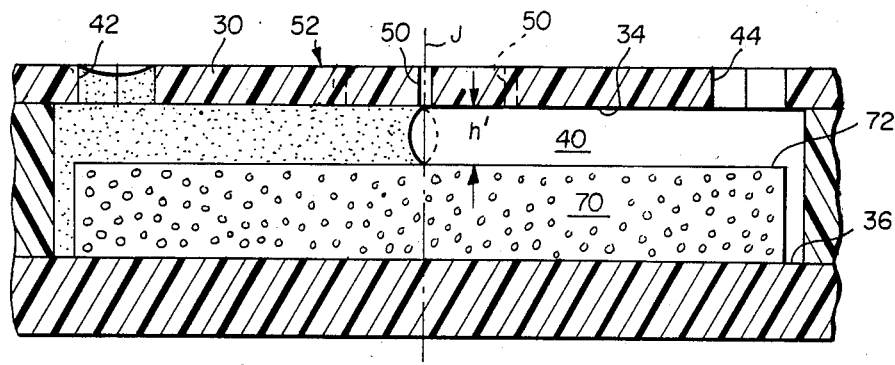
FIG. 4 is a fragmentary section view similar to that of FIG. 3, except after the two liquids have met at the junction J.

To admit the two liquids into passage 40, access apertures 42 and 44, FIGS. 1–3, are formed in member 30. These apertures preferably have a shape that includes at least one corner to insure that a drop of liquid deposited by a metering device, not shown, on exterior surface 46, FIG. 2, approximately at one of the apertures, will enter the aperture and thus passage 40. Most preferably, the apertures are shaped for this purpose in the manner described in U.S. Pat. No. 4,254,083, issued Mar. 3, 1981. The contents of the '083 patent are expressly incorporated herein by reference. As shown in FIG. 1, a hexagon is a particularly useful flow-through shape for apertures 42 and 44.

Apertures 42 and 44 are further given a void volume that insures that the metered volume of liquid L, FIG. 3, will contact both surface 34 and layer 70 to initiate capillary flow. Most preferably, the volume of liquid L is about 10 $\mu l$.

To vent entrapped air from passage 40 as the two liquids move toward each other, one or more apertures 50, FIGS. 1 and 3, are formed in member 30, approximately centered between apertures 42 and 44. Apertures 50 are much smaller, e.g., 1 mm or less, than apertures 42 and 44 because they do not need the volume capability of the latter.

Thus, passage 40 transports the liquids toward each other in the portion 52, FIGS. 1 and 3, extending between apertures 42 and 44. When the liquids contact each other in the vicinity of apertures 50, they form an ionic connection, the first part of the ionic circuit needed for ion measurement by the electrometer. Thus, frame 12 functions as an ion bridge.

Arm portions 54 of passage 40 extend from bridge portion 52 to apertures 60 which communicate with ISE's 14, thus giving to passage 40 a horseshoe shape.

For ease in manufacturing, and because of the control provided by the water-swellable composition hereinafter discussed, passage 40 is preferably free of fibers.

In accordance with one aspect of the invention, FIGS. 1–4, there is provided in portion 52 of the device, means for increasing the viscosity of the liquid as it flows through portion 52 from access aperture 42 or 44. Any such means will suffice, as long as it provides a decrease in the ratio of water to high molecular weight materials or solids of the aqueous liquid, and still maintains flow of the liquid within the capillary space. In the preferred embodiment wherein portion 52 is an ion bridge fluidly connecting two ISE's, the means is also inert to the two liquids that flow through portion 52. Such viscosity-increasing means reduces the liquid flow rate, and overcomes the tendency, when two liquids are present, of the liquid with the higher surface tension forcing the liquid with the lower surface tension out of portion 52.

Preferably, the viscosity-increasing means comprises a water-swellable composition placed in the form of a layer 70, or two layers (not shown) on one or both of the surfaces 34 and 36, preferably on surface 36. Most preferably, FIG. 3, layer 70 extends a sufficient portion of the length of portion 52 between apertures 42 and 44 so as to underlie those apertures. A capillary spacing h, FIG. 3, is provided between top surface 72 of layer 70, and opposing surface 34 of member 30. When flow is complete in portion 52, the capillary spacing is reduced to h', FIG. 4. Because capillary spacing h is only gradually reduced during liquid flow through portion 52, there is ample volume initially to provide a more rapid withdrawal of liquid from access apertures 42 and 44 than would be the case if the capillary spacing were fixed at h'.

Useful examples of water-swellable compositions include hardened and unhardened gelatin; gelatin containing non-ionic surfactants; water-swellable materials known to be substitutes for gelatin, such as gelatin derivatives, e.g., acetylated gelatin, phthalated gelatin, and the like; polysaccharides such as dextran; starch; gum arabic; agarose; zein; casein; pectin; collagen derivatives; collodion; agar-agar; arrowroot; cellulose derivatives such as those hardened by ethanol-free silicic acid as described in *Research Disclosure* Pub. 20431, published April, 1981, by Industrial Opportunities Ltd., Homewell, Havant, Hampshire, PO9 1EF, United Kingdom; high molecular weight polyvinyl alcohol or polyvinylpyrrolidone; N-isopropylacrylamide; water-swellable polymers and copolymers as described in U.S. Pat. No. 4,203,442, e.g., poly(N-vinyl lactam); and mixtures of the aforesaid materials. Gelatin is most preferred, and when used, any form is useful, for example, gelatin from ox hides, ox bones, and pig hides. Various non-ionic surfactants are useful in the gelatin, depending upon the flow rate that is desired. Useful examples of surfactants include nonylphenoxypolyglycidol surfactant available from Olin Manufacturing under the tradename "10G", and octylphenoxy polyethoxyethanol surfactants available from Rohm and Haas under the trade names "X-100" and "X-405". Preferably, the surfactant is present in an amount of from 0.05 weight % to about 2.5 weight %. Most preferably, the amount of surfactant is from 0.08 weight % to 0.15 weight %, for example, 0.005 g/m². Hardened gelatin is particularly useful to control by impeding the amount of swelling. In such embodiments conventional hardeners are useful, for example, bisvinylsulfonylmethyl ether, hereinafter "BVSME." The amount of hardener that is selected depends on which hardener is used, and how much swell is desired from the composition.

Alternatively, ionic surfactants are useful in the composition if the device is to be used other than in testing ionic analytes.

One advantage in using gel-like materials for layer 70 is that they are self-leveling. This insures that capillary spacing h and h' will be maintained without unduly restricting the manufacturing process by requiring severe manufacturing tolerances.

Useful water-swellable compositions include the above-noted materials overcoated with other materials to form a second layer. Useful examples of overcoat materials include (a) poly(n-isopropylacrylamide-coacrylamide), and (b) a beaded layer prepared as described in U.S. Pat. No. 4,258,001. The details of the beaded layers of the last-named patent are hereby incorporated by reference. A useful example of such a beaded layer comprises beads of poly(vinyltoluene-co-p-t-butylstyrene-co-methacrylic acid) with or without an adhesive such as poly(n-butyl acrylate-co-styrene-co-2-acrylamide-2-methylpropane sulfonic acid) or poly(methylacrylate-co-2-acrylamido-2-methylpropane sulfonic acid-co-2-acetoacetoxyethyl methacrylate). Both of these materials (a) and (b) are useful to decrease the amount of swell that the composition would otherwise undergo. The beaded layer provides the further property of delaying the onset of swell. Such delay is useful in insuring that the liquid first rapidly enters passage 40, thereby reducing the risk that protruding liquid will spill out of access apertures 42 or 44.

Still further, sponges are alternatively useful as the material of layer 70, if they have a known amount and rate of expansion when placed in contact with an aqueous liquid, and are provided with pore sizes that prevent absorption of the predominant solids (the cells, in the case of whole blood, and protein in the case of serum). In addition to water-swellable compositions, useful embodiments of the invention include materials that are not water-swellable compositions. For example, a coating can be used of compounds that rapidly dissolve in the liquid being transported during the time of flow required for the liquid to travel to the intended junction, provided the selected compound also gives a sufficient increase in viscosity of the liquid as to reduce the rate of flow of the liquid. The preferred examples are non-ionic compounds for which dissolution of the amount of compound used is sufficiently rapid as to occur within less than 15 seconds, and preferably 2 to 3 seconds. For example, hydroxyethyl cellulose in one case, and hydroxypropyl cellulose in another case, each having a weight-average molecular weight of between about 100,000 and about 300,000, when coated in an amount of about 1.3 mg/cm² was sufficiently soluble in serum, that is, is dissolved in said 2 to 3 seconds.

An advantage of the layer 70 of this invention is that it increases the viscosity without drawing into itself so much of the water of the liquid that air pockets form in the liquid flow through the spacing h or h'. That is, the increase in viscosity is achieved by the preferential absorption by layer 70 of $H_2O$, compared to high molecular weight material and solids, at a rate of absorption equal to or less than the rate of swelling. Thus, the loss of $H_2O$ volume (by absorption) equals or is less than the loss of volume in the void of passage 40 due to the reduction of spacing h to h'. By such means, liquid flow is maintained continuous through this portion 52 of the passage, at a reduced rate. In contrast, if layer 70 were a rigid, porous matrix, such as a fibrous matrix, it would likely absorb both the water component of the liquid as well as the solids, depending on the pore size. As a result, the viscosity would not be increased because the liquid-to-solids ratio would not change.

The percent reduction in the effective capillary spacing that is available from the swelling of the layer 70 depends upon a number of factors. These include the kind of material, e.g., the kind of polymer selected, the thickness of layer 70, and the original effective capillary spacing prior to swelling. Preferably, these are selected such that, at the time when the menisci $M^1$ and $M^2$ of the two liquids meet at their junction, schematically indicated as a line J representing a plane transverse to portion 52, FIGS. 3 and 4, the original spacing h, FIG. 3, will be reduced at least about 25% to spacing h', FIG. 4. If whole blood is the liquid being assayed, most preferably the swelling will not reduce the spacing more than 50% within the time of the test (usually about 3 minutes), so that h' will accommodate the cellular fraction.

If other liquids such as serum are being assayed, the 50% reduction limit is not necessary. That is, a final reduction in h greater than 50% but less than 100% is also useful for liquids such as serum. Capillary spacing h' must not be completely eliminated, as otherwise errors in the potentiometric readings tend to occur, presumably because the flow of ions necessary to the potentiometric measurement for the ISE test is hindered by the swollen composition.

One method of determining whether the viscosity has been increased sufficiently comprises the steps of adding, via apertures 42 and 44, two liquids having a difference in surface tensions of about 4 dynes/cm. Enough is added to fill bridge portion 52. After a time of about three minutes, if the junction J has not moved, the increase in viscosity is adequate, at least in pinning down the junction for liquids having this much difference in surface tensions. (To render easier the observation of the junction, a small amount of dye can be added to either liquid.)

With regard to the water-swellable compositions described above, I have found that an adequate increase in viscosity is obtained by causing a reduction in capillary spacing h that is between about 35% and about 50% by the time the junction (line J) is reached. I have found that such a reduction in capillary spacing insures that the increase in liquid viscosity resulting from absorption of water into layer 70, provides sufficient resistance against any significant displacement of the junction between the liquids during the time of the test (about 3 minutes). As noted above, it is believed the swelling achieves this result by removing water from the sample, thereby increasing the percent concentration of high molecular weight material and solids, and therefore viscosity. The increased viscosity in turn resists the displacement force causing the unwanted displacement of one liquid by the other.

Figure 6:
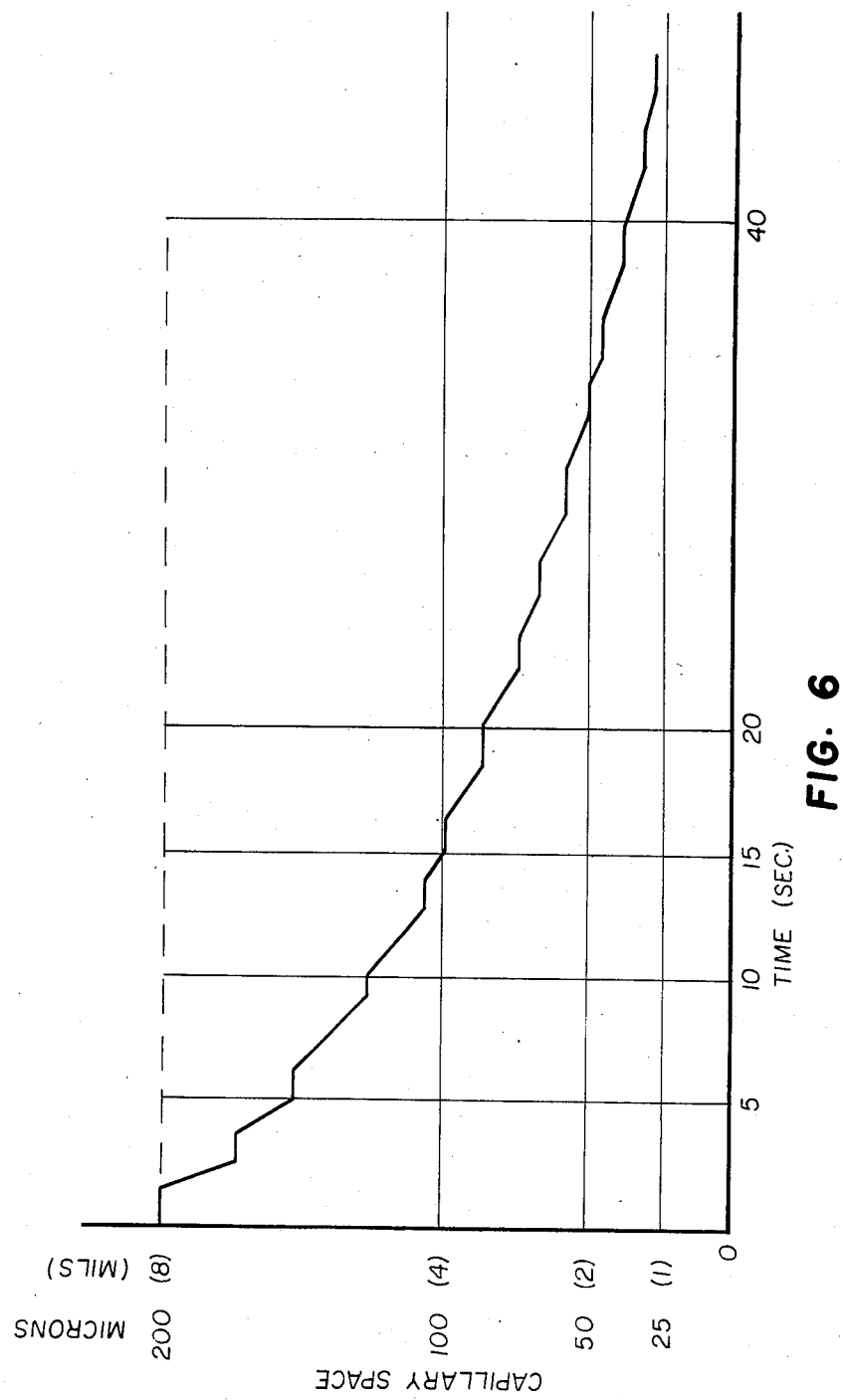
FIG. 6 is a graph of the height of the capillary space above one useful swellable composition, versus the time of addition of the liquid to the layer.

FIG. 6 is a plot of the swelling characteristics of a bridge constructed as described above, when tested with H$_2$O at a pH of about 7.0. As shown, initial capillary spacing h between layer 70 and top surface 34 is about 200$\mu$, for a layer 70 having an initial thickness of about 18$\mu$ and a composition of unhardened deionized gelatin containing Olin 10G surfactant in an amount of about 0.01 g/m$^2$. For such a bridge, swelling proceeds over time as shown, using water as the liquid. From curve 10 on this graph, it is apparent that, when the time of contact reaches 15 seconds, spacing h is reduced by 100 microns to 100 microns, a 50% reduction. From this graph the effect of other initial spacings h can be deduced by preparing a tracing of the curve as an overlay and moving the portion of the tracing at time=0 to the desired initial capillary spacing. For example, if the initial spacing h is 400 microns, in 15 seconds the composition swelling reduces that value 25% to 300 microns. At the end of three minutes, such composition will have reduced the 400 microns initial spacing to a little over 200 microns, or a reduction that does not exceed 50%.

The following Table I sets forth the swelling ability as a "final" swell %, of other water-swellable compositions, in the presence of water only, that is, after about three minutes. The % is calculated as follows: (Final composition thickness—original composition thickness)÷original composition thickness.

TABLE I

| Sample | Material | % Swell |
|--------|----------|---------|
| A | Gelatin of FIG. 6, to which has been added 2 wt % hardener (BVSME) | 173 |
| B | Gelatin of FIG. 6, to which has been added 3 wt % hardener (BVSME) | 67 |
| C | Gelatin of FIG. 6, except that the same surfactant was used in an amount of 1.0 g/m$^2$, rather than 0.01 g/m$^2$ | 303 |
| D | Gelatin of FIG. 6, followed by an overcoat of poly(n-isopropylacrylamide-co-acrylamide) in an amount of 1.0 g/m$^2$ | 246 |

The "% swell" figures of Table I will vary as the pH, ionic strength, and percent proteins of the aqueous liquid varies, as is well known. For example, as the percent of proteins in the liquid increases, the amount of swelling caused by the liquid decreases. The factors of pH, ionic strength and % protein may also affect the rate of swelling, but to a lesser extent.

As will be readily apparent, the initial thickness t of layer 70, as well as its composition, are selected to be commensurate with the initial spacing h and the amount of reduction of h that is desired from such swelling.

Alternatively, and in accord with another aspect of the invention, the thickness of the initial capillary spacing and of the swellable composition, and the material of the composition, are selected to control the rate of flow of the liquid within bridge portion 52. Specifically, the swell rate is selected so that the liquid flows half the distance between apertures 42 and 44 (i.e, to about the line J) in a time of from 2 seconds to about 15 seconds. It is this reduced flow rate that tends to insure that the first liquid will not race the full length of portion 52 before the second liquid is deposited into the other aperture.

The reduction in the half-distance flow rate is conveniently combinable with a 50% reduction in the capillary spacing by the time the junction, located generally at J, is reached. In FIG. 6, the 50% reduction point is reached at 100$\mu$, or 15 seconds. If the flow time to the 50% reduction is desired to be only 12 seconds, then the initial spacing h should be reduced to about 170 microns, as 85 microns will remain after about 12 seconds, using the same swelling profile.

Various materials are useful as member 30, opposite layer 70. For example, polystyrene, cellulose acetate butyrate and cellulose triacetate available from Eastman Kodak Co. under the trademark "Kodacel", are useful.

Referring again to FIG. 2, arm portions 54 of passage 40 are constructed, as described in my U.S. application Ser. No. 362,930, filed Mar. 29, 1982, and entitled "Liquid Transport Device Providing Diversion of Capillary Flow into a Non-Vented Second Zone", now U.S. Pat. No. 4,473,457, issued Sept. 25, 1984, to permit apertures 60 to be circular in shape. For purposes of completeness, the aspects which permit such apertures to be used will now be described. The diverting aperture 60 is formed by sidewalls 61 that extend from surface 36 of member 32 to exterior surface 13. Sidewalls 61 generally provide a flow-through width dimension and a flow-through length dimension which, in the case of circular embodiments, comprise the diameter. In addition, aperture 60 includes a dimension (diameter) that extends in a direction that parallels width w of zone portion 54. Aperture 60 is most preferably centered between sidewalls 41 and 43 and is fluidly connected to an aperture 62 formed in and surrounded by adhesive layer 15. Thus, apertures 60 and 62 provide a second passage extending from the intersection of sidewalls 61 with surface 36, to the surface of layer 16 exposed by aperture 62 in the adhesive layer. The length of such second passage is the distance $t_0$ equal to the sum of $t_1$ and $t_2$. Thickness $t_1$ is the thickness of member 32 at aperture 60 and $t_2$ is the thickness of adhesive layer 15 at aperture 62 (the distance between surface 13 of member 32 and the surface of layer 16).

The second passage formed by apertures 60 and 62 preferably has no air vent.

Adequate flow of liquid to the terminal surface of layer 16 occurs if the proper value of liquid head $h''$ is selected for a given value of $t_0$, and the proper first passage width w is selected for the parallel dimension of the aperture. That is, for a given set of conditions, the head $h''$ is an empirically determinable function of $t_0$. This function appears to be dependent on the surface tension of the liquid flowing in the device, the contact angle that liquid forms with the materials comprising the members of the first passage, and the relative value of the flow-through width of the diverting aperture, compared to the flow-through width of the first passage at that aperture. The exact expression of the function and the mechanism causing it are not completely understood for all conditions, although a specific embodiment is hereinafter described. In such an embodiment, member 32 has a surface 36 adjacent aperture 60 that is a relatively nonwettable material, with a contact angle greater than or equal to 85°. If $h''$ is sufficiently large for a given $t_0$, and the flow-through widths are properly selected as described hereinafter, the liquid in bridge portion 54 advances to contact the surface of layer 16 before the liquid completely surrounds aperture 60 in its continued flow in passage 40. If all other factors are held constant, the greater the distance $t_0$, the greater the value $h''$ must be to provide the energy that insures this contact with layer 16 will occur before the liquid flow in passage 40 surrounds the aperture.

Once contact is achieved with the surface of layer 16, the meniscus moves on to fill up aperture 60.

The ability of the liquid to wet a given material for members 30 and 32 will tend to alter how much head $h''$ is needed for a given thickness $t_0$, as will the surface tension of the liquid. For example, the greater the wettability of surface 34 compared to surface 36, the more the meniscus edge at surface 34 "leads" its edge at surface 36. The greater this disparity, the greater the pressure that the head $h''$ tends to apply, and the greater the distance that is useful for $t_0$. Furthermore, the value of $h''$ for a given thickness $t_0$ also depends on the resistance to first passage flow provided by the diverting aperture. If the width w of passage portion 54, FIG. 1, is much greater than the flow-through dimension (width or length) of aperture 60 that is parallel to w, the liquid will act as though the aperture were not there, and surround aperture 60 before it contacts layer 16. On the other hand, if the flow-through width of the first passage only equals the parallel dimension of the diverting aperture, the resistance to flow into the diverting aperture is increased to the point where the device is inoperative. More specifically, if aperture 60 is, for example, rectangular with a flow-through length extending parallel to the width w of the first passage, dimensioned to equal that width w, liquid flow in passage 40 will not readily proceed into aperture 60.

Therefore, the resistance to first passage flow created by the diverting aperture, the advancing contact angles for the materials used, and the liquid surface tension must be considered in determining the value of $h''$ for a given $t_0$.

For one preferred embodiment, the surface of member 30 is selected from materials that provide a contact angle, for the liquid to be used, of between about 60° and about 80°, as described above. The ratio of width w of passage 40 to the parallel dimension of aperture 60 is between about 1.1 to 1 and about 1.5 to 1. Stated reversely, the parallel dimension of the diverting aperture is between about 0.65 and about 0.9 of the first passage flow-through width. Care is taken to center aperture 60 between sidewalls 41 and 43, as otherwise the range of ratios noted above for the parallel dimension of the aperture and the first flow-through width will not accurately reflect the conditions needed for proper flow. More specifically, insufficient clearance of the aperture along one wall and a large clearance at the opposite sidewall permits liquid to flow too readily past the aperture through the large clearance, and the aperture becomes surrounded by the liquid. Finally, the terminating surface of layer 16 is selected so as to have an advancing contact angle less than about 85°, and a receding contact angle no greater than about 30°, to prevent the liquid from de-wetting at the electrode. De-wetting tends to lead to aperture 60 becoming surrounded and air being entrapped in the second passage.

Thus, particularly useful devices include those in which at least surface 34 of member 30 is cellulose triacetate, at least surface 36 of member 32 is polystyrene, aperture 60 is circular, the ratio of width w to the diameter of aperture 60 is about 1.28 to 1.0, and layer 16 is a cellulose acetate overcoat of a chloride electrode as described in the aforesaid U.S. Pat. No. 4,199,411. Preferred diameters of aperture 60, in such embodiments, range between about 2.0 mm and about 5.0 mm, provided that the width w of passage 40 is modified to provide the 1.28 to 1 ratio noted above. For such an embodiment, the relationship between $h''$ and $t_0$ such that satisfactory wetting of the ISE occurs, is $h'' \geq 150 + 0.87\, t_0$, measured in microns. Since it is desired that, for good capillary flow, $h''$ should not exceed about 600$\mu$, then $t_0$ in such an embodiment does not exceed about 515$\mu$.

The surface of layer 16 need not be adhered directly to member 32, in order that the diverting aperture 60 should function as described. That is, useful embodiments include those in which the exposed surface of layer 16 is spaced a short distance from the apertured member 32 by an intervening wall member.

To allow venting of air entrapped ahead of liquid advancing along arm portions 54, an air vent 56, FIG. 2, is provided, fluidly connecting each arm of zone 40 with one of the windows 22. Vent 56 preferably has a greatly reduced flow-through diameter, for example, 75 microns or less, to minimize gas-liquid interchange in the liquid under test. For example, if the ISE's 14 and 14' are chosen to test for $CO_2$ (or $HCO_3^{\ominus}$), then it is undesirable that a large surface area of the liquid should be exposed to the air.

Figure 5:
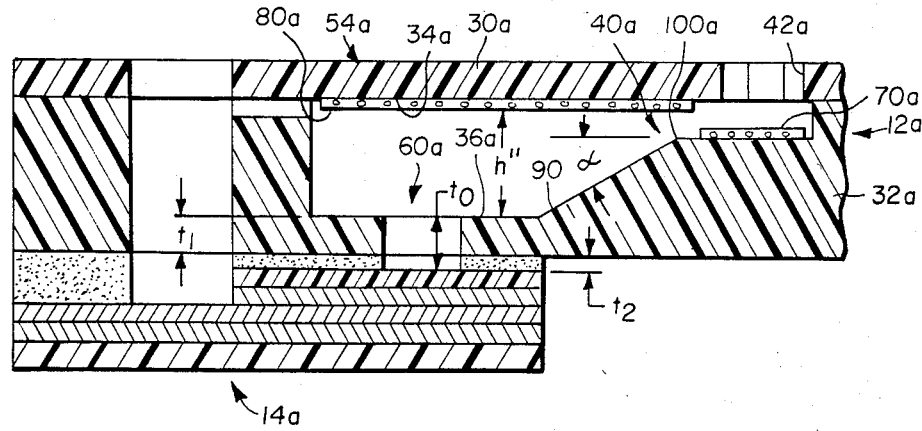
FIG. 5 is a fragmentary section view similar to that of FIG. 2, but illustrating an alternate embodiment of the invention.

In the embodiment of FIG. 5, the arm portions of the bridge have been modified to include a water-swellable composition as a means of positively forcing the liquid into the diverting aperture. Parts similar to those previously described bear the same reference numeral to which the distinguishing suffix "a" has been appended. Thus, frame 12a comprises members 30a and 32a providing an interior capillary transport passage 40a accessed via aperture 42a, that is fluidly connected via aperture 60a to ISE 14a, as before. Layer 70a provides controlled flow within bridge portion 52a as before, and the ratio $h''/t_0$ is selected as described above. However, an additional layer 80 of a water-swellable composition, optionally of a material different from that of layer 70, is deposited on at least one of the surfaces 34a and 36a, most preferably surface 34a. Its function is to swell as liquid advances within portion 54a, and thus act in cooperation with the ramp 90 commencing at edge 100a. That is, ramp 90 is effective to provide a gradual increase in spacing $h''$, with increased distance from aperture 42a. As layer 80a swells, the liquid is pressured to flow more rapidly, ramp 90 being effective to urge the increased flow towards aperture 60a and ISE 14a.

Alternatively, layer 80 extends over only that part of surface 36a that is directly above aperture 60a. In such a case, when it swells, layer 80 acts to drive the liquid into aperture 60a, more than acting to drive it away from access aperture 42a.

EXAMPLES

The following Examples further illustrate the invention.

In each of the following examples, a bridge similar to the bridge portion 52, FIG. 3, was simulated by applying a layer of water-swellable composition onto a support, using the thicknesses T noted in Table II, and laminating to that layered support, enough double-sided adhesive tapes to build up the desired capillary spacing, except for Example 2. In Example 2, a shim of plastic having a 25μ thickness was physically held in place by downwardly applied pressure, without the use of adhesive. The covering member in all cases was 100 micron-thick cellulose triacetate, provided with a circular access aperture of a diamater of about 3 mm. The test was conducted by applying more than enough human serum to the access aperture to provide flow within the passage for the time t'. The times t' were estimated based upon the swell profile curves, similar to FIG. 6, that were obtained for each of the compositions. The serum had a surface tension of between 35 and 45 dynes/cm². Two replicates were run for each sample, except for Examples 2 and 3. Final swollen thicknesses were determined, based upon the swell percentages noted in Table I, assuming a "final" test time of 3 minutes. Variances in distances traveled for time t' were mostly due to variances in the horizontal width of the capillary spacing—i.e., the width varied from about 2.54 mm to about 3.8 mm, from replicate to replicate.

TABLE II

| Ex. No. | Nature of Swellable Composition | Initial Composition Thickness (T, FIG. 3) | Initial Capillary Spacing (h, FIG. 3) | Time t' to Reduce h by 50% | Distance Serum Traveled in Time t' | | | Final Swollen Thickness of Composition |
|---|---|---|---|---|---|---|---|---|
| | | | | | 1st Replicate | 2nd Rep. | Average | |
| 1 | Gelatin evaluated in FIG. 6 | 17.8μ | ≃200μ | ≃15 sec | 5.84 cm* | 5.46 cm* | 5.65 cm | ≃195μ |
| 2 | A of Table I | 14.0μ | ≃25μ | ≃7 sec | 2.54 cm | not measured | 2.54 cm | ≃38μ** |
| 3 | B of Table I | 10.2μ | ≃25μ | ≃7 sec | not measured | → | → | ≃17μ |
| 4 | C of Table I | 15.7μ | ≃50μ | ≃10 sec | 3.05 cm | 2.41 cm | 2.73 cm | ≃63μ |
| 5 | D of Table I | 12.7μ | ≃50μ | ≃15 sec | 3.18 cm | 3.56 cm | 3.37 cm | ≃44μ |

*In these replicates, flow actually stopped before time t' had elapsed. However, because serum thereafter could be withdrawn from the capillary passage with a cotton swab, it was clear that swelling had not eliminated the capillary spacing to cause the stoppage.
**This is possible because the total distance available for swelling was T + h, here equal to 39μ.

As will be readily apparent, the half-distance of a bridge prepared as in Example 1 should be about 5.65 cm, so that the total distance between apertures 42 and 44 would be about 11.3 cm. For Examples 2, 4 and 5, the total distance between the two access apertures should be, respectively, about 5.1 cm, 5.5 cm and 6.7 cm, in order that the half-distance flow times will be the indicated times t' (between 2 and about 15 sec). Such total distances can be reduced, particularly for Example 5, and still produce a half-distance flow rate that is between 2 and about 15 sec.

The invention has been described in detail with particular reference to preferred embodiments thereof, but it will be understood that variations and modifications can be effected within the spirit and scope of the invention.

What is claimed is:

1. In a liquid transport device for simultaneously transporting two different aqueous liquids within a capillary passage, said device comprising two opposed liquid transport surfaces spaced apart a distance effective to induce capillary flow between said surfaces of introduced liquid and to create the capillary passage;
    and access means, including two apertures, for respectively admitting said different liquids to said passage from the exterior of the device to two spaced-apart regions of the passage;
    the improvement wherein there is disposed on at least one of said surfaces, spaced a capillary distance from the other surface, control means for (a) increasing the viscosity of the liquid while it is flowing past said at least one surface, and (b) at the same time maintaining such flow continuous within said passage,
    whereby the rate of flow within said passage is reduced and any displacement force created when two liquids with unequal surface tensions meet within said passage, is countered.

2. A device as defined in claim 1, wherein said control means comprises a water-swellable composition disposed on said at least one surface.

3. In a liquid transport device for simultaneously transporting two different aqueous liquids within a capillary passage, said device comprising two opposed liquid transport surfaces spaced apart a distance effective to induce capillary flow between said surfaces of introduced liquid and to create the capillary passage;

and access means, including two apertures, for respectively admitting said different liquids to said passage from the exterior of the device to two spaced-apart regions of the passage;

the improvement wherein a water-swellable composition is disposed on at least one of said surfaces, between said regions so as to predeterminedly constrain, by swelling, liquid flow within said passage between said regions to a reduced, non-zero rate.

4. The invention defined in claim 2 or 3, wherein (1) said regions are spaced, and (2), said composition is water-swellable, by an amount and at a rate such that the liquid introduced at one region travels one-half the distance between said regions in a time of from 2 seconds to about 15 seconds.

5. In a liquid transport device for simultaneously transporting two different liquids within a capillary passage, said device comprising two opposed liquid transport surfaces spaced apart a distance effective to induce capillary flow between said surfaces of introduced liquid and to create the capillary passage;

and access means, including two apertures, for simultaneously admitting liquids to said passage from the exterior of the device, a portion of said passage between said apertures being constructed to bring together at a junction between the apertures, two such liquids introduced to said passage, the improvement wherein a water-swellable composition is disposed on at least one of said surfaces, between said apertures to form an initial capillary spacing between said composition and the other of said surfaces, said passage between said apertures having a predetermined length and said composition being water-swellable by an amount and at a predetermined rate such that said initial capillary spacing is reduced by at least about 25% by the time liquid introduced into one of said apertures flows to said junction.

6. A device as defined in claim 3 or 5, wherein said composition comprises a material selected from the group consisting of gelatin, a gelatin derivative, starch, polysaccharide, hydrogel, gum arabic, agarose, zein, casein, pectin, a derivative of collagen, collodion, agar-agar, arrowroot, polyvinyl alcohol, polyvinyl pyrrolidone, a cellulose derivative, and a mixture of any of said materials.

7. In an ion bridge fluidly connecting at least two ion-selective electrodes comprising the reagents operative to provide a determination of the activity of an ionic analyte in a liquid having a surface tension between about 25 and about 75 dynes/cm$^2$, said bridge comprising two opposed liquid transport surfaces spaced apart a distance effective to induce capillary flow between said surfaces of introduced liquid and to create a transport passage, said passage having portions that are in separate liquid communication with each of said electrodes;

and access means, including two apertures, for respectively admitting liquids from the exterior of said bridge to two spaced-apart regions of the passage;

the improvement wherein there is disposed on at least one of said surfaces, spaced a capillary distance from the other surface, control means for (a) increasing the viscosity of the liquid while it is flowing past said at least one surface, and (b) at the same time maintaining such flow continuous within said passage, whereby the rate of flow within said passage is reduced and any displacement force created when two liquids with unequal surface tensions meet within said passage, is countered.

8. A bridge as defined in claim 7, wherein said control means comprises a water-swellable composition disposed on said at least one surface.

9. In an ion bridge fluidly connecting at least two ion-selective electrodes comprising the reagents operative to provide a determination of the activity of an ionic analyte in a liquid having a surface tension between about 25 and about 75 dynes/cm$^2$, said bridge comprising two opposed liquid transport surfaces spaced apart a distance effective to induce capillary flow between said surfaces of introduced liquid and to create a transport passage, said passage having portions that are in separate liquid communication with each of said electrodes;

and access means, including two apertures, for respectively admitting liquids from the exterior of said bridge to two spaced-apart regions of the passage;

the improvement wherein a water-swellable composition is disposed on at least one of said surfaces, between said regions so as to predeterminedly constrain, by swelling, liquid flow within said passage between said regions to a reduced, non-zero rate.

10. A bridge as defined in claim 8 or 9, wherein (1) said regions are spaced, and (2), said composition is water-swellable, by an amount and at a rate such that the liquid introduced at one region travels one-half the distance between said regions in a time of from 2 seconds to about 15 seconds.

11. A bridge as defined in claim 9, wherein said composition swells at a rate such that there is a reduction of about 50% in said initial capillary spacing by the time the liquid has traveled said one-half distance.

12. In an ion bridge fluidly connecting at least two ion-selective electrodes comprising the reagents operative to provide a determination of the activity of an ionic analyte in a liquid having a surface tension between about 25 and about 75 dynes/cm$^2$, said bridge comprising two opposed liquid transport surfaces spaced apart a distance effective to induce capillary flow between said surfaces of introduced liquid and to create a transport passage, said passage having portions that are in separate liquid communication with each of said electrodes;

access means, including two apertures, for admitting liquids to said passage from the exterior of said bridge, a portion of said passage between said apertures being constructed to bring together at a junction two such liquids introduced to said passage each through a respective separate one of said apertures, the improvement wherein a water-swellable composition is disposed on at least one of said surfaces, between said apertures to form an initial capillary spacing between said composition and the other of said surfaces, said passage between said apertures having a predetermined length and said composition being water-swellable by an amount and at a predetermined rate such that said initial capillary spacing is reduced by at least about 25% by the time liquid introduced into one of said apertures flows to said junction.

13. A bridge as defined in claim 9 or 12, wherein said passage portions providing liquid communication with said each electrode include means in said surfaces defining a diverting aperture terminated by one of said electrodes, said composition being disposed on at least that part of one of said surfaces that is opposite to said diverting aperture, whereby said composition of said passage portion, when contacted with an aqueous liquid, acts to drive the liquid towards the respective electrode.

14. A bridge as defined in claim 9 or 12, wherein said passage portions providing liquid communication with said each electrode are characterized by a spaced-apart distance having a value that increases with increased liquid-flow distance from said access aperture, said composition being disposed on at least one of said surfaces that provides said increasing spaced-apart distance.

15. A bridge as defined in claim 9 or 12, wherein said composition comprises a material selected from the group consisting of gelatin, a gelatin derivative, starch, polysaccharide, hydrogel, gum arabic, agarose, zein, casein, pectin, a derivative of collagen, collodion, agar-agar, arrowroot, polyvinyl alcohol, polyvinylpyrrolidone, a cellulose derivative, and a mixture of any of said materials.

16. A bridge as defined in claim 15, and further including a surfactant admixed with said material.

17. A bridge as defined in claim 9 or 12, wherein, over a period of about 3 minutes, said composition is swellable by an amount no greater than that which reduces the volume of said passage in the vicinity of said composition, by 50%, whereby whole blood is capable of flowing within said passage without being blocked by composition swell.

18. In a liquid transport device for simultaneously transporting two different aqueous liquids within a capillary passage, said device comprising two opposed liquid transport surfaces spaced apart a distance effective to induce capillary flow between said surfaces of introduced liquid and to create the capillary passage;

and access means, including two apertures, for respectively admitting said different liquids to said passage from the exterior of the device to two spaced-apart regions of the passage;

the improvement wherein there is disposed on at least one of said surfaces, spaced a capillary distance from the other surface, control means for (a) increasing the viscosity of the liquid while it is flowing past said at least one surface, and (b) at the same time maintaining such flow continuous within said passage, said control means being effective to increase said viscosity during liquid flow by at least an amount sufficient, over a time period of about 3 minutes, to prevent displacement of the junction formed between two liquids, having a difference in surface tension of about 4 dynes/cm, that are introduced into said passage via said apertures.

19. A device as defined in claim 18, wherein said control means comprises a water-swellable composition disposed on said at least one surface.

20. In an ion bridge fluidly connecting at least two ion-selective electrodes comprising the reagents operative to provide a determination of the activity of an ionic analyte in a liquid having a surface tension between about 25 and about 75 dynes/cm$^2$, said bridge comprising two opposed liquid transport surfaces spaced apart a distance effective to induce capillary flow between said surfaces of introduced liquid and to create a transport passage, said passage having portions that are in separate liquid communication with each of said electrodes;

and access means, including two apertures, for respectively admitting liquids from the exterior of said bridge to two spaced-apart regions of the passage;

the improvement wherein there is disposed on at least one of said surfaces, spaced a capillary distance from the other surface, control means for (a) increasing the viscosity of the liquid while it is flowing past said at least one surface, and (b) at the same time maintaining such flow continuous within said passage, said control means being effective to increase said viscosity during liquid flow by at least an amount sufficient, over a time period of about 3 minutes, to prevent displacement of the junction formed between two liquids, having a difference in surface tension of about 4 dynes/cm, that are introduced into said passage via said apertures.

21. A bridge as defined in claim 20, wherein said control means comprises a water-swellable composition disposed on said at least one surface.

* * * * *